US010052436B2

(12) United States Patent
Högdahl (10) Patent No.: US 10,052,436 B2
(45) Date of Patent: Aug. 21, 2018

(54) AUTOMATIC INJECTION DEVICE

(71) Applicant: Carebay Europe Ltd, Swatar (MT)

(72) Inventor: Stefan Högdahl, Stockholm (SE)

(73) Assignee: Carebay Europe Ltd, Sliema (MT)

( * ) Notice: Subject to any disclaimer, the term of this patent is extended or adjusted under 35 U.S.C. 154(b) by 696 days.

(21) Appl. No.: 14/422,474

(22) PCT Filed: Aug. 7, 2013

(86) PCT No.: PCT/EP2013/066542
§ 371 (c)(1),
(2) Date: Feb. 19, 2015

(87) PCT Pub. No.: WO2014/029621
PCT Pub. Date: Feb. 27, 2014

(65) Prior Publication Data
US 2015/0217057 A1    Aug. 6, 2015

Related U.S. Application Data (60) Provisional application No. 61/691,529, filed on Aug. 21, 2012.

(30) Foreign Application Priority Data

Aug. 20, 2012  (SE) ...................... 1250934

(51) Int. Cl.
*A61M 5/20*    (2006.01)
*A61M 5/24*    (2006.01)
(Continued)

(52) U.S. Cl.
CPC ............ *A61M 5/2033* (2013.01); *A61M 5/24* (2013.01); *A61M 5/326* (2013.01); *A61M 5/46* (2013.01);
(Continued)

(58) Field of Classification Search
CPC ........ A61M 5/2033; A61M 5/24; A61M 5/46; A61M 5/326; A61M 2005/2437;
(Continued)

(56) References Cited

U.S. PATENT DOCUMENTS

| | | | | |
|---|---|---|---|---|
| 5,599,309 A | * | 2/1997 | Marshall | A61M 5/2033 604/117 |
| 2008/0154200 A1 | | 6/2008 | Lesch | |
| 2011/0202011 A1 | * | 8/2011 | Wozencroft | A61M 5/2033 604/192 |

FOREIGN PATENT DOCUMENTS

| | | |
|---|---|---|
| EP | 2364739 A1 | 9/2011 |
| WO | 94/13342 A1 | 6/1994 |

(Continued)

OTHER PUBLICATIONS

EPO, Int'l Search Report in PCT/EP2013/066542, dated Dec. 10, 2013.
EPO, Written Opinion in PCT/EP2013/066542, dated Dec. 10, 2013.

*Primary Examiner* — Imani Hayman
*Assistant Examiner* — Lauren P Farrar
(74) *Attorney, Agent, or Firm* — Piedmont Intellectual Property (57) ABSTRACT

A medicament injection device arranged to receive a replaceable container subassembly includes front and rear housings releasably connectable to each other. A reloadable drive mechanism is accommodated in the rear housing for acting on the plunger of a replaceable container subassembly for expelling medicament. A needle hider front is slidably arranged within the front housing. A needle shield remover is arranged to connect with a needle shield of the replaceable container subassembly and to be removably inserted into a proximal end of the front housing through the needle hider front. The needle shield remover is adapted to interact with (Continued)

the reloadable drive mechanism such that a user can reload the drive mechanism.

13 Claims, 8 Drawing Sheets

(51) Int. Cl.
*A61M 5/46* (2006.01)
*A61M 5/32* (2006.01)

(52) U.S. Cl.
CPC ..... *A61M 5/3204* (2013.01); *A61M 2005/202* (2013.01); *A61M 2005/206* (2013.01); *A61M 2005/208* (2013.01); *A61M 2005/2407* (2013.01); *A61M 2005/2437* (2013.01); *A61M 2005/2488* (2013.01)

(58) Field of Classification Search
CPC .... A61M 2005/2407; A61M 2005/208; A61M 2005/2488; A61M 2005/202; A61M 5/3204; A61M 2005/206
See application file for complete search history.

(56) References Cited

FOREIGN PATENT DOCUMENTS

| WO | 2007/036676 A1 | 4/2007 |
| WO | 2009/087355 A1 | 7/2009 |
| WO | 2010/023481 A1 | 3/2010 |

* cited by examiner

AUTOMATIC INJECTION DEVICE

FIELD OF THE INVENTION

The present invention relates to an injection device, especially a reusable auto injector.

BACKGROUND OF THE INVENTION

Reusable auto injectors which can be loaded with a container subassembly, such as a syringe, are known in the prior art. U.S. Pat. No. 5,599,309 discloses an auto injector for use with proprietary syringes. That prior art discloses a device comprising a drive member that receives the rear end of a plunger of a syringe and a trigger for releasing the drive member such that a medicament can be injected. Drawbacks with that prior art are that needle is outside the device and visible to the user after the device has been removed from the injection site and that the re-loading is complicated and time consuming.

SUMMARY OF THE INVENTION

It is therefore an object of the invention to provide an injection device with improved user friendliness. In particular, it is an object of the present invention to provide an injection device where the needle is kept non-visible to the user at all times and that the device is easily re-loadable. This object and other objects are solved by an injection device as defined in claim 1. This object and other objects are also solved by a method as defined in claim 15. Preferred embodiments of the present invention are defined in the dependent claims.

Thus, in accordance with an aspect of the present invention, there is provided a medicament injection device having a proximal end and a distal end and being arranged to receive a replaceable container subassembly having a medicament container with a plunger therein, a needle and a needle shield. The medicament injection device comprises a front housing and a rear housing which are releasably connectable to each other and a reloadable drive mechanism is accommodated in the rear housing for acting on the replaceable container subassembly. The reloadable drive mechanism is moveable between a cocked and an extended position and a release mechanism is provided for releasing the drive mechanism from said cocked position to said extended position. A needle hider front is slidably arranged within the front housing. A needle shield remover is arranged to connect with a needle shield of the replaceable container subassembly received in the reloadable medicament injection device, wherein the needle shield remover is arranged to be removably inserted into a proximal end of the front housing through the needle hider front. The needle shield remover, when inserted into the front housing is adapted to be used to interact with the reloadable drive mechanism accommodated in said rear housing such that a user can re-locate the reloadable drive mechanism from said extended position to said cocked position. By designing a needle shield remover and the front housing having a needle hider front such that needle shield remover together with the front housing can be used for reloading the drive mechanism, the use of the device is simplified and improved to a large extent. A user simply has to release the front housing from the rear housing, replace the needle shield remover and then turn the front housing 180 degrees and use the needle shield remover to push the drive mechanism from its proximal, extended position to its distal, cocked position. By providing a needle hider front at the proximal end of the front housing, the needle can be kept out of sight of a user. Many users prefer not to see the needle, neither during use, nor when the device is not used.

In accordance with an embodiment of the medicament injection device according to the invention, a needle hider body is arranged within the front housing and the needle hider front is adjustably connected to the needle hider body by means of a threaded connection. This assures that the needle is kept out of sight at all times.

In accordance with an embodiment of the medicament injection device according to the invention, the needle shield remover and the needle hider front are arranged to mate with each other such that axial movement of the needle shield remover relative to the needle hider front is allowed while rotation of the needle shield remover relative to the needle hider front is prevented. This arrangement allows a user to use the needle shield remover to adjust the axial position of the needle hider front which is connected by a threaded connection to the needle hider body by holding the front housing while turning the needle shield remover.

In accordance with an embodiment of the medicament injection device according to the invention, the needle hider body is axially moveable within the front housing between a proximal end position and a distal end position and wherein a syringe guide is arranged within said needle hider body for receiving a replaceable container subassembly, said syringe guide being axially moveable between a proximal end position and a distal end position relative to the front housing and wherein a proximal end surface of the syringe guide defines a maximum insertion depth for the needle shield remover. The proximal end surface of the syringe guide defines the maximum insertion depth of the needle shield remover and acts as an abutment such that the front housing can be used to relocate the drive mechanism in the rear housing.

In accordance with an embodiment of the medicament injection device according to the invention, a first biasing member is arranged between the syringe guide and the needle hider body. This first biasing member biases the syringe guide towards said distal end position and the needle hider body towards said proximal end position. The first biasing member ensures that the needle hider moves out and covers the needle as soon as the injection device is removed from the injection site such that the needle never will be visible to the patient.

In accordance with an embodiment of the medicament injection device according to the invention, a resilient syringe collar is arranged at a distal end of the syringe guide, said resilient syringe collar being adapted to receive and hold a replaceable container subassembly. The resilient syringe collar, made from e.g. rubber, will make sure that the replaceable container subassembly is firmly held in place while still being replaceable.

In accordance with an embodiment of the medicament injection device according to the invention, the front housing comprises internal abutment surfaces defining said proximal end positions and distal end positions for the needle hider body and the syringe guide relative to the front housing.

In accordance with an embodiment of the medicament injection device according to the invention, the penetration depth of a needle of a container subassembly received in the reloadable medicament injection device is adjusted by adjusting the position of the needle hider front. The threaded connection of the needle hider front to the needle hider body is a simple solution providing an adjustable penetration depth.

In accordance with an embodiment of the medicament injection device according to the invention, the needle hider front comprises indication means presenting a set needle penetration depth. The indication means can be in the form of numerals visible in a window or opening in the front housing clearly indicating the currently set penetration depth.

In accordance with an embodiment of the medicament injection device according to the invention, the needle shield remover comprises flexible hook means arranged to grasp the needle shield of a replaceable container subassembly received in the reloadable medicament injection device. When the needle shield remover is inserted into the proximal end of the front housing through the needle hider front the flexible hook means will deflect over the outer surface of the needle shield and as soon as the flexible hook means passes the distal end of the needle shield they will flex back to a less biased position and the hook means, preferably provided with a fluke, or barbed element, will securely grasp the needle shield such that when the needle shield remover is pulled out of the front housing, the needle shield will be pulled off the container subassembly received in the medicament injection device.

In accordance with an embodiment of the medicament injection device according to the invention, the reloadable drive mechanism comprises an axially moveable plunger rod driver and a drive spring biasing the plunger rod driver towards the proximal end position. The plunger rod driver and the rear housing comprise corresponding guide means for guiding the plunger rod driver during movement within the rear housing. By providing the drive mechanism and its components in the rear housing, and since the rear and front housings are separable, reloading of the drive mechanism is simplified.

In accordance with an embodiment of the medicament injection device according to the invention, the plunger rod driver is configured to act on the plunger of the replaceable container subassembly for moving axially said replaceable container subassembly in relation to the front housing such that said needle is penetrated and said medicament is expelled through said needle. Obviously, it is understandable that the plunger rod driver is configured to act directly on the plunger when the plunger rod driver may comprise a plunger rod or indirectly through a plunger rod which is part of the container subassembly.

In accordance with an embodiment of the medicament injection device according to the invention, the rear housing comprises a button blocker moveable within the rear housing between a proximal end position, in which the button blocker prevents the release mechanism from releasing the drive mechanism from said cocked position to said extended position, and a distal end position, in which the button blocker allows the release mechanism to release the drive mechanism from said cocked position to said extended position, wherein the button blocker is moved from said proximal end position to said distal end position when the needle hider body is axially moved within the front housing from said proximal end position to said distal end position. This means that the button blocker is released only when the needle hider body is pushed towards a distal end position, e.g. when the medicament injection device is pushed against a patient's skin, which ensures that the medicament injection device is not inadvertently discharged.

In accordance with an embodiment of the medicament injection device according to the invention, a second biasing member is provided within the rear housing biasing the button blocker towards said proximal end position. This ensures that as soon as the plunger rod driver is pushed back to its distal end position, the button blocker will assume its proximal end position where release of the drive mechanism is prevented.

In accordance with another aspect of the present invention, there is provided a method for reloading a medicament injection device according to the first aspect of the invention. There, a user removes the front housing from the rear housing having the needle shield remover arranged at the front housing through the needle hider front, and brings the proximal end of the needle shield remover in contact with a proximal end of the reloadable drive mechanism accommodated in said rear housing and subsequently moves the reloadable drive mechanism from said extended position to said cocked position by pushing said front housing and said needle shield remover axially towards said rear housing and said drive mechanism.

BRIEF DESCRIPTION OF THE DRAWINGS

The invention will now be described in more detail and with reference to the appended drawings in which.

DESCRIPTION OF PREFERRED EMBODIMENTS

As used herein, the term "container" encompasses all types of containers suitable for injectable liquid composition. Concerning the terms "distal" and "proximal" they refer to points which are further away and closer to the injection site respectively.

Figure 1A:
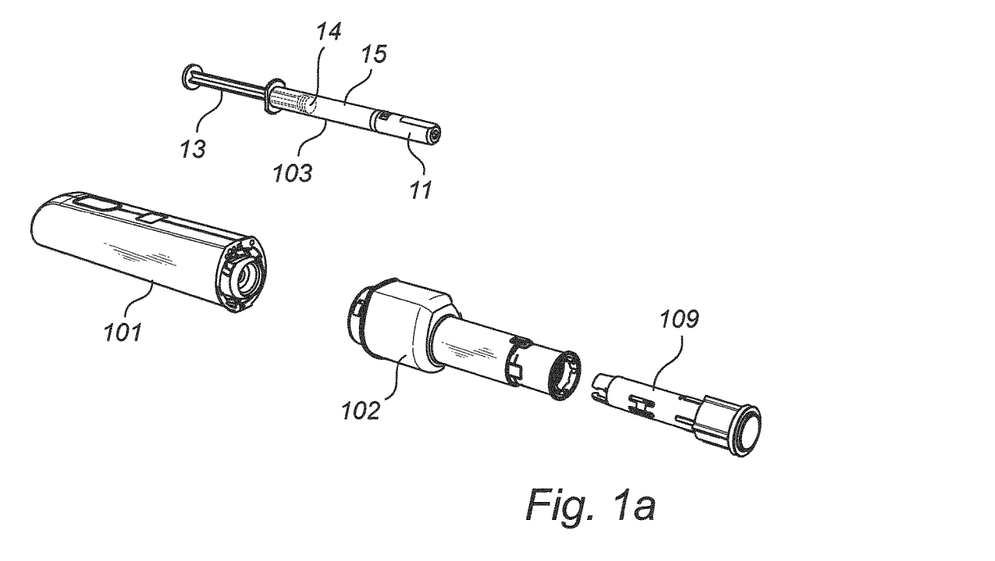
FIG. 1a is a schematic perspective view of an embodiment of the medicament delivery device according to the invention in a disassembled state.
Figure 1B:
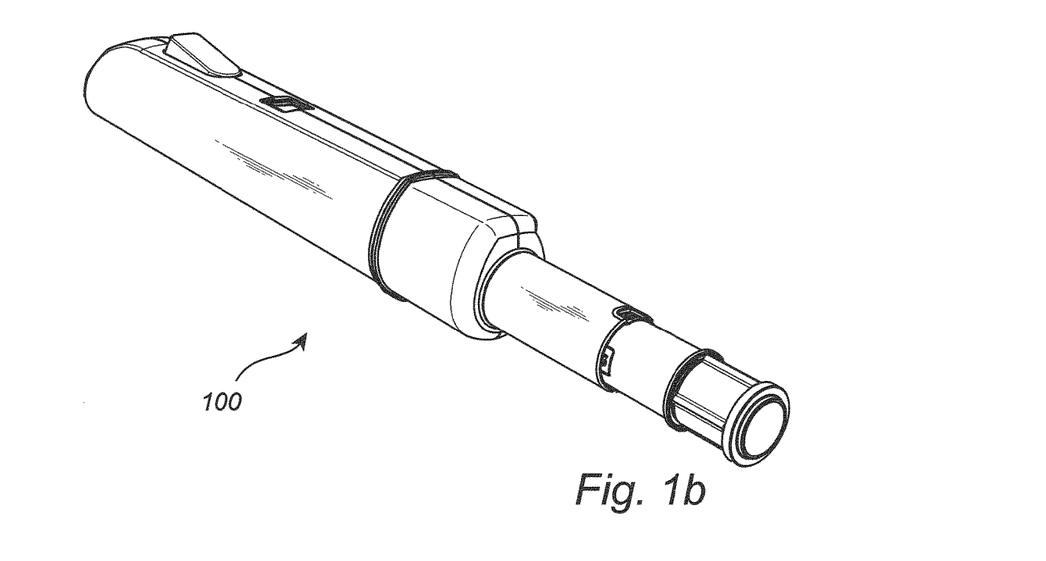
FIG. 1b is a schematic perspective view of an embodiment of the medicament injection device according to the invention in an assembled state.

In a first embodiment of a medicament delivery device 100 according to the invention, as shown in FIGS. 1a and 1b, a medicament injection device 100 comprises a rear housing 101 made from e.g. thermoplastic, a front housing 102 and a replaceable container subassembly 103, such as a syringe. The rear and front housings 101, 102 are connectable to each other by e.g. a twisting coupling. Typically, the front and rear housings 101, 102 can be connected and disconnected by a 90 degree relative twist of the housings 101, 102. The replaceable container subassembly 103 may comprise a needle (not shown in FIG. 1a), a medicament container 15, a plunger 14, a plunger rod 13 and a needle shield 11 arranged to protect users from the needle. Obviously, it is also imaginable that the container subassembly 103 lacks a plunger rod 13 and that this plunger rod is part of the device.

Figure 2A:
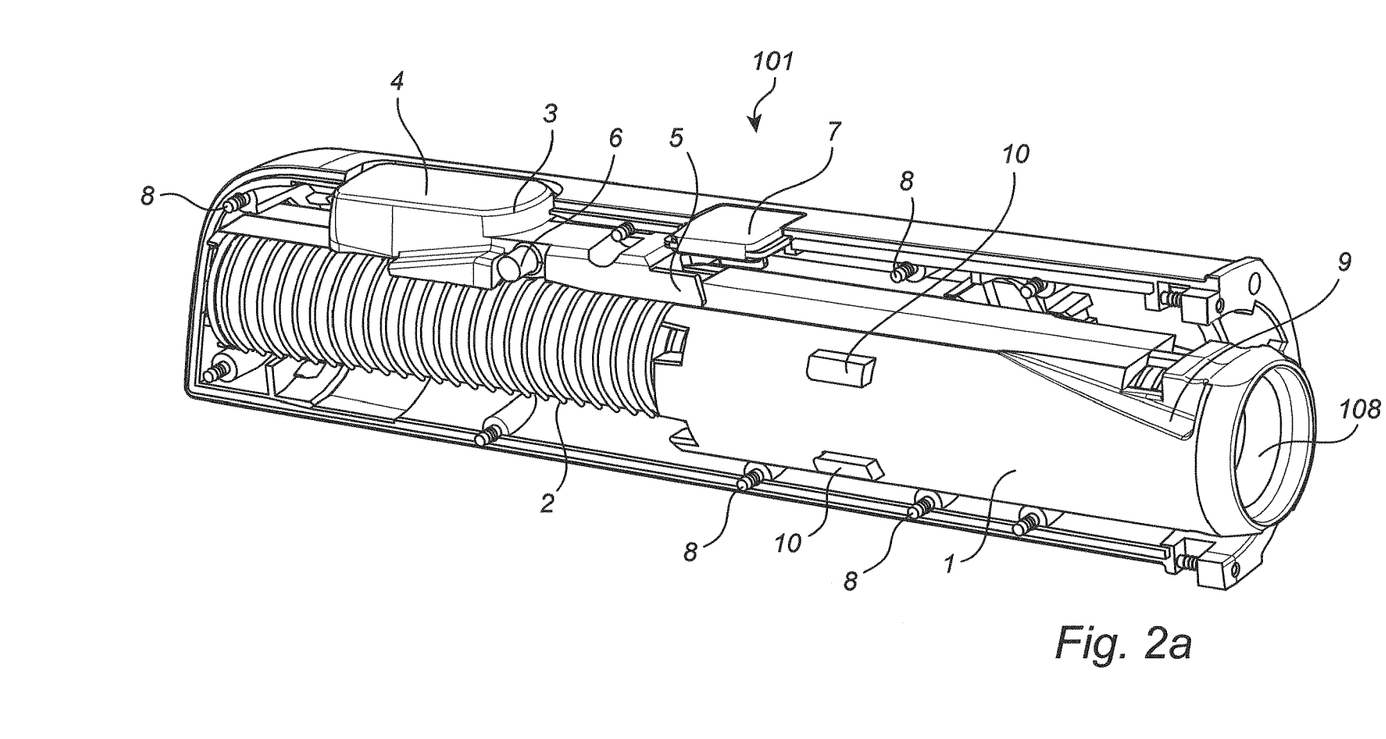
FIG. 2a is a schematic exploded perspective view of an embodiment of the rear housing of the medicament injection device according to the invention.
Figure 2B:
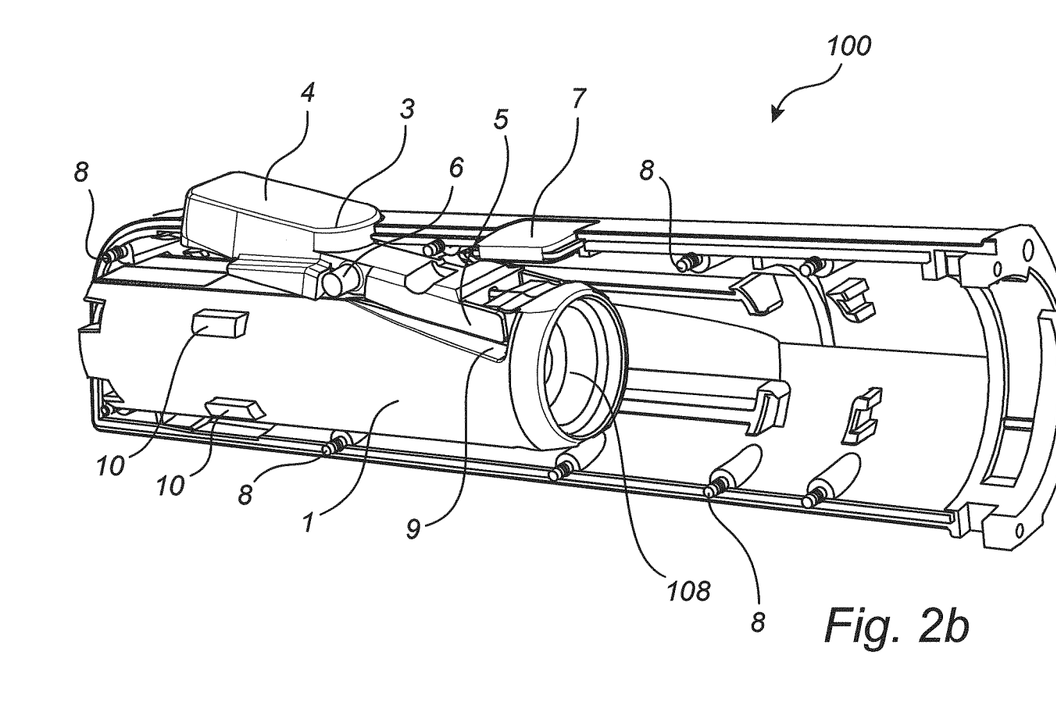
FIG. 2b is a schematic exploded perspective view of an embodiment of the rear housing of the medicament injection device according to the invention.

FIGS. 2a and 2b disclose the rear housing 101 comprising the drive mechanism 108. The drive mechanism 108 comprises a plunger rod driver 1 arranged axially moveable within the rear housing 101 between a proximal end position (shown in FIG. 2a) and a distal end position (shown in FIG. 2b). The proximal end position of the plunger rod driver 1 corresponds to a position where the plunger rod 13 and the plunger 14 of the replaceable container subassembly 103 have been pressed to the end of its stroke, i.e. the medicament container 15 has been emptied, and the distal end position of the plunger rod driver 1 corresponds to a position where the plunger rod 13 and the plunger 14 of the replaceable container subassembly 103 have not yet been moved, i.e. the medicament container 15 is full. The drive mechanism 108 further comprises a drive spring 2, here in the form of a helical coil spring, which biases the plunger rod driver 1 towards its proximal end position. A release mechanism 3 for releasing the plunger rod driver 1 of the drive mechanism 108 from the distal, or cocked, position to the proximal, or extended, position is arranged at an upper surface of the rear housing 101. The release mechanism 3 is pivotable around a pivoting axle 6 between an extended position (shown in FIG. 2b) and a depressed position (shown in FIG. 2a) and comprises a trigger button 4 and an abutment member 5 which abuts and interworks with the plunger rod driver 1. In FIG. 2a, the release mechanism 3 has been depressed and the plunger rod driver 1 has adopted its extended, proximal end position. In this position the abutment member 5 abuts an upper surface of the plunger rod driver 1 and prevents the release mechanism 3 from pivoting back around pivot axle 6. The design of the details imply that as long as the plunger rod driver 1 is not in its distal end position, the release mechanism 3 cannot assume its extended position but is instead locked in the depressed position. A resilient member (not shown in the figures) is provided biasing the trigger button 4 towards its extended position which means that when the interaction between the plunger rod driver 1 and the release mechanism 3 allow for it, i.e. when the abutment member 5 of the release mechanism 3 reaches recess 9 in the plunger rod driver 1, the release mechanism 3 will assume its extended position (see FIG. 2b). Adjacent, or at least near, the release mechanism 3 a status window 7 is arranged through which symbols provided on the plunger rod driver 1 are visible to indicate the status of the medicament delivery device 100. The status window is preferably made of a transparent, or at least translucent, plastic material. The rear housing 101 can be made up of two halves which are secured to each other by means of pins or projections 8 provided at one of the halves and corresponding openings 8' (not shown in FIG. 2a or 2b) in the other halves. Obviously, other solutions are imaginable, such as tongue and groove solutions; snap catch elements; or even permanent securing with welding or gluing. Interacting guide means 10 are provided on an outer surface of the plunger rod driver 1 and an internal surface of the rear housing 101 guiding the plunger rod driver 1 during its movement within the rear housing 101.

Figure 3:
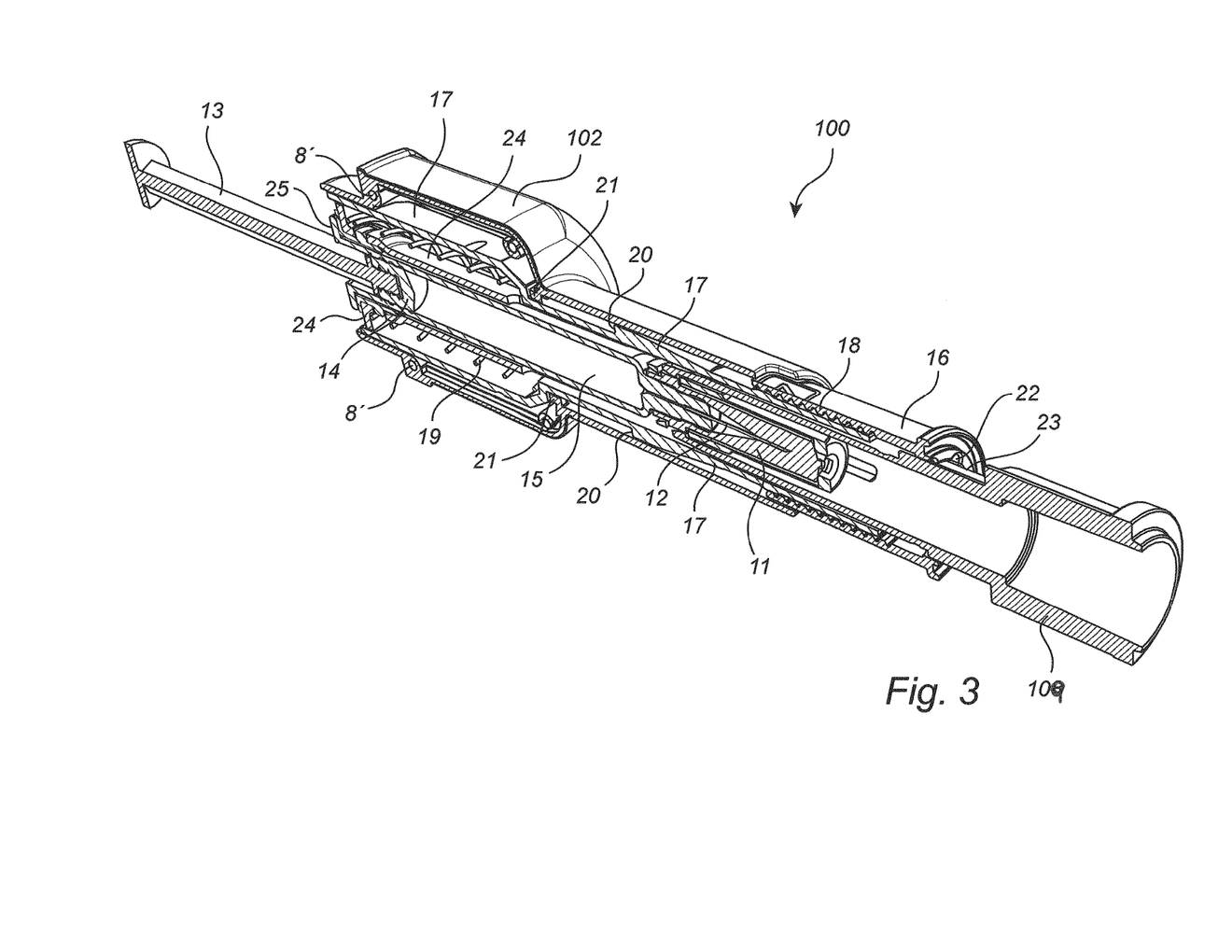
FIG. 3 is a schematic perspective cross-section of an embodiment of the front housing of the medicament injection device according to the invention.

FIG. 3 shows a cross-section of a front housing 102 provided with a replaceable container subassembly in the form of a syringe 103 and a needle shield remover 109 partially arranged at a proximal end of the front housing 102 and grasping a needle shield 11 encompassing a needle 12 of syringe 103. The syringe 103 further comprises a plunger rod 13, a plunger 14 and a medicament container 15. A needle hider front 16 is provided at a proximal end of the front housing connected to a needle hider body 17 by means of a threaded connection 18, more specifically the needle hider front 16 is provided on the needle hider body 17. The needle shield remover 109 comprises a proximal and a distal end, wherein the distal end is arranged at the proximal end of the front housing 102 through the needle hider front 16. The threaded connection 18 provides a user with a possibility of adjusting the penetration depth of needle 12 during use. The needle hider body 17 extends through the inside of the front housing 102 and encompasses the syringe 103. The purpose of the needle hider body 17 and the needle hider front is to hide the needle from a user, both during and between uses of the device. The needle hider body 17 and front housing 102 are provided with corresponding abutment surfaces 20, 21 which define the distal and proximal end positions of the axial movement of needle hider body 17 relative to the front housing 102. This relative axial movement in combination with the adjustability of the needle hider front 16 ensures that the needle 12 is kept non-visible at all time. A syringe guide 24 is arranged within front housing 102, more specifically within the needle hider body 17, axially moveable between a distal end position and a proximal end position relative to the front housing 102. The proximal end position is defined by corresponding abutment surfaces (not shown) provided on an internal surface of the front housing 102 and on the external surface of the syringe guide 24 respectively. The abutment surfaces provided on the front housing 102 and on the syringe guide 24 will typically have to extend through openings or slots provided in the needle hider body 17 in order to connect with each other. These abutment surfaces in combination with the adjustable needle hider front 16 determine the penetration depth of needle 12 during use of the device. The needle shield remover 109 is configured to be partially inserted i.e. axially movable into the proximal end of the front housing 102 through the needle hider front 16 and through the needle hider body 17. The axial movement of the needle shield remover when inserted into the proximal end of the front housing 102 is stopped by the interaction between the abutment surfaces of the syringe guide 24 and of the needle shield remover 109, more specifically the proximal end of the syringe guide and the distal end of the needle shield remover 109, while the abutment surfaces between the front housing 102 and the syringe guide 24 serve to prevent the syringe guide from moving distally relative to the front housing 102. A resilient syringe collar 25, typically made of rubber, is arranged at a distal end of the syringe guide 24 for receiving and holding the syringe 103. The resilient material will securely hold the syringe in place while still allowing it to be replaced after it has been emptied. Normally, the resilient syringe collar 25 will stay in its position in the syringe guide during replacement of the syringe but can of course be exchanged if necessary. A first biasing member 19 is arranged between the syringe guide 24 and the needle hider body 17 which biases the syringe guide 24 towards its distal end position and the needle hider body 17 towards its proximal end position. The first biasing member 19 ensures that as soon as the device according to the invention is removed from the injection site, the needle hider body, and thus also the needle hider front 16, automatically travel outwards keeping the needle 12 out of sight to a user. The front housing 102 can be made up of two halves which are secured to each other by means of pins or projections 8 (not shown in FIG. 3) provided at one of the halves and corresponding openings 8' in the other halves. Obviously, other solutions are imaginable, such as tongue and groove solutions; snap catch elements; or even permanent securing by welding or gluing.

Figure 4:
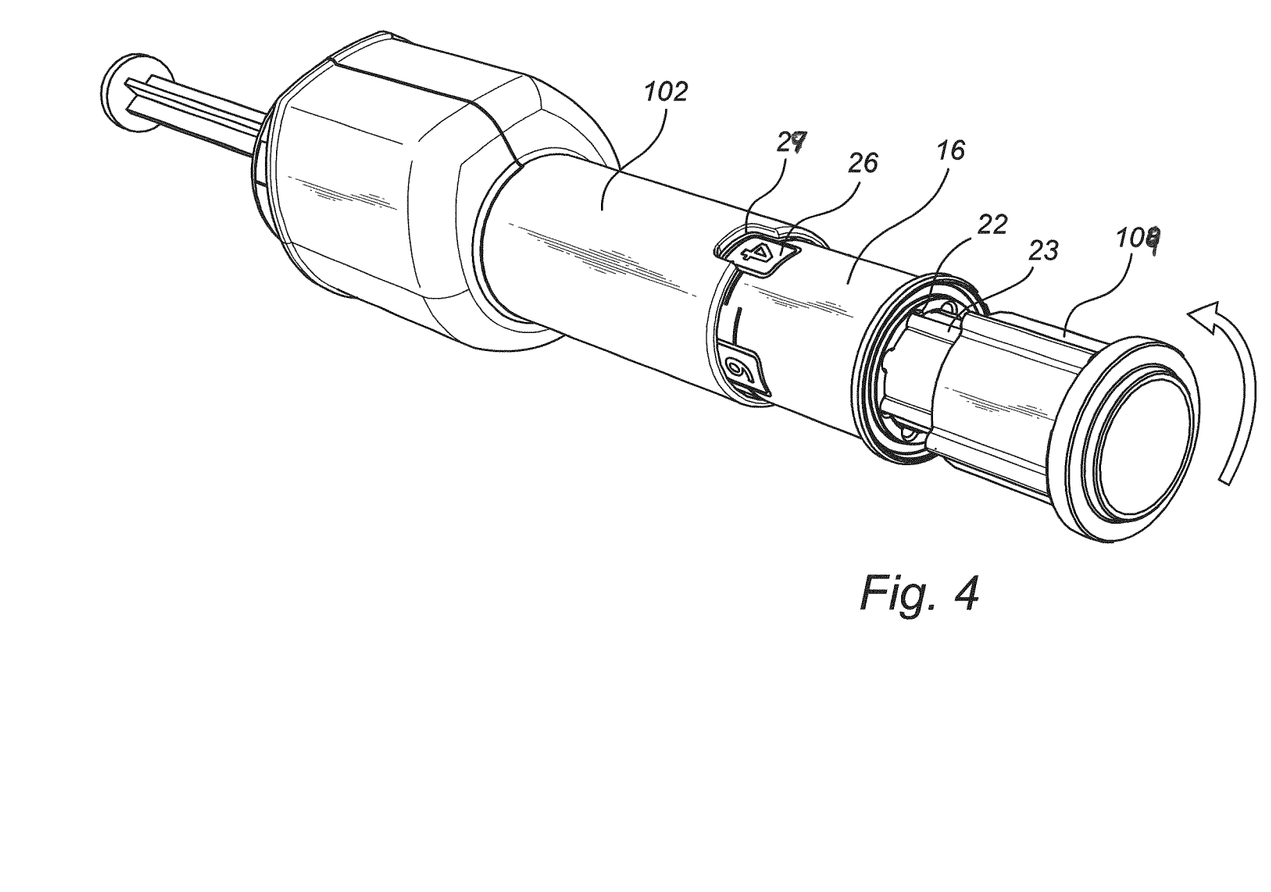
FIG. 4 is a schematic perspective view of an embodiment of the front housing of the medicament injection device according to the invention.

In FIG. 4 the easiness of adjusting the penetration depth of needle 12 is displayed. Needle shield remover 109 is provided with axially running protrusions 23 having a corresponding shape to recesses 22 provided in the needle hider front 16. This means that the needle shield remover 108 can be inserted axially into needle hider front 16 while any relative rotational movement between the two is prevented. By using the needle shield remover 109 as a grip element, a user can adjust the position of the needle hider front 16 relative to the needle hider body 17 by turning, thus setting the penetration depth of the needle 12 during use. The front housing 102 and/or the needle hider body 17 may be provided with means defining a number of pre-set positions which snap in place when the needle hider front 16 is turned. The needle hider front 16 is provided with digits 26 visible in a cut-out, window 29 or similar provided at the front housing 102 indicating a set penetration depth. The penetration depth can be adjusted back and forth until a desired value has been set.

Figure 5A:
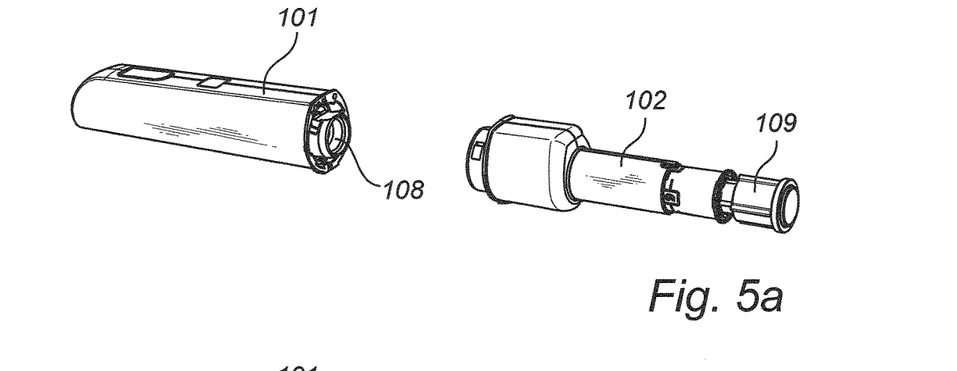
FIGS. 5a and 5b is a schematic perspective view of method steps according to the invention.
Figure 5B:
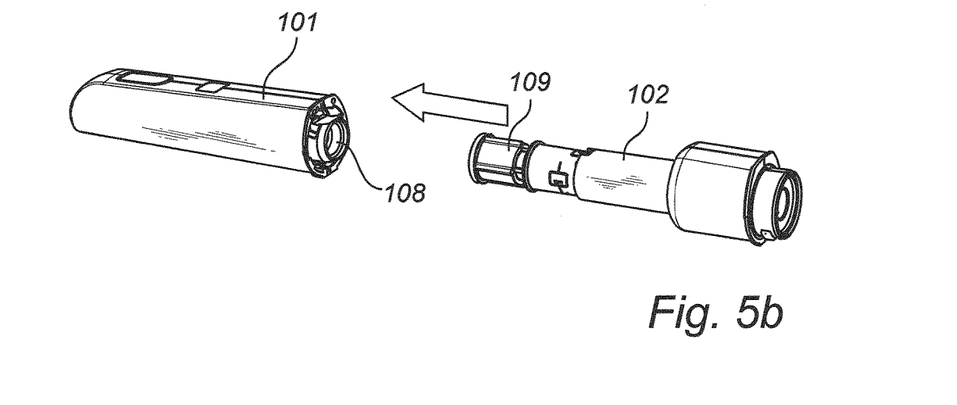

FIGS. 5a and 5b schematically show how the drive mechanism of the device 100 is reloaded. The front housing 102 having the needle shield remover 109 attached at its front end through the needle hider front 16 is removed from the rear housing 101 by twisting the housings 90 degrees relative to each other. Then, the proximal end of the needle shield remover 109, is positioned abutting the drive mechanism 108 arranged in the rear housing 101 and situated in its proximal end position. Thereafter, the front housing together with the needle shield remover 109 is used to force the drive mechanism 108 towards its proximal end position where it will snap into a cocked position, ready to be used. A more detailed explanation of the functioning of the device will be provided with respect to FIGS. 6a, 6b, 7a and 7b below.

Figures 6A, 6B:
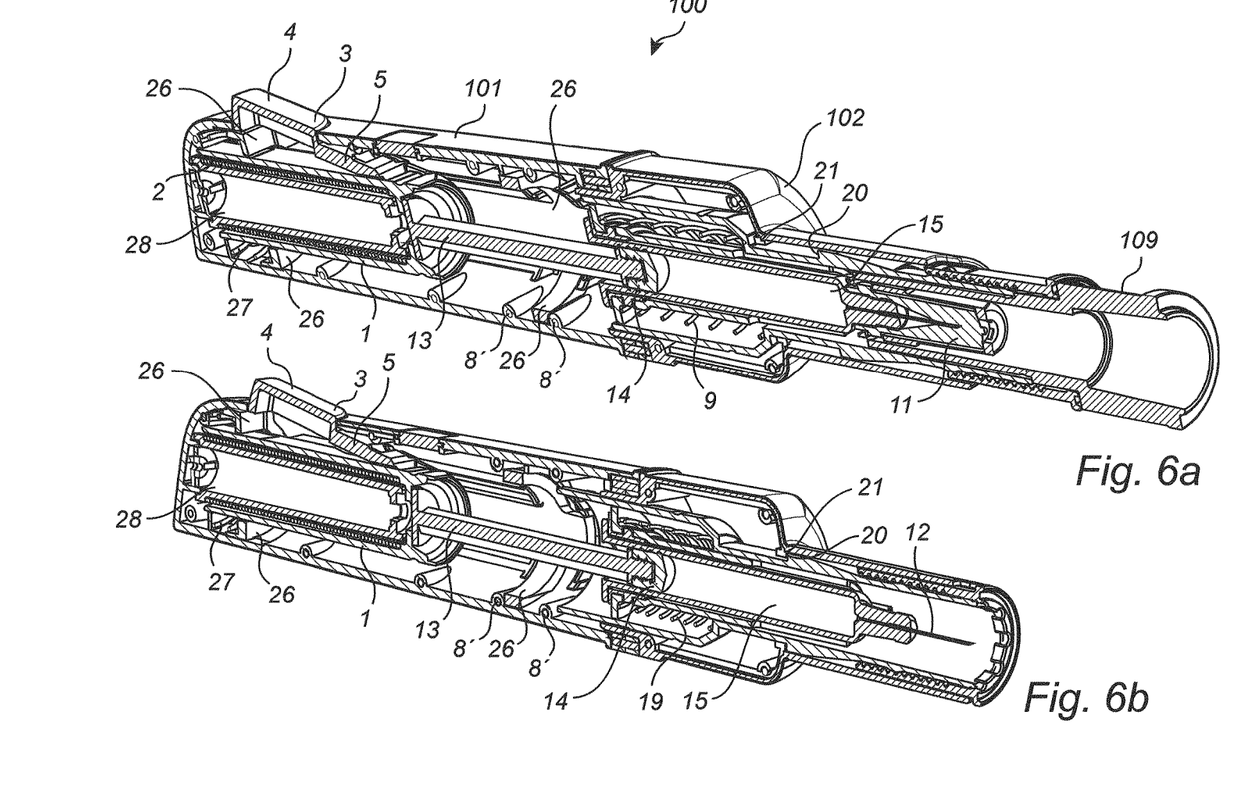
FIGS. 6a, 6b, 7a and 7b are schematic perspective cross-sections of an embodiment of the medicament injection device according to the invention.
Figures 7A, 7B:
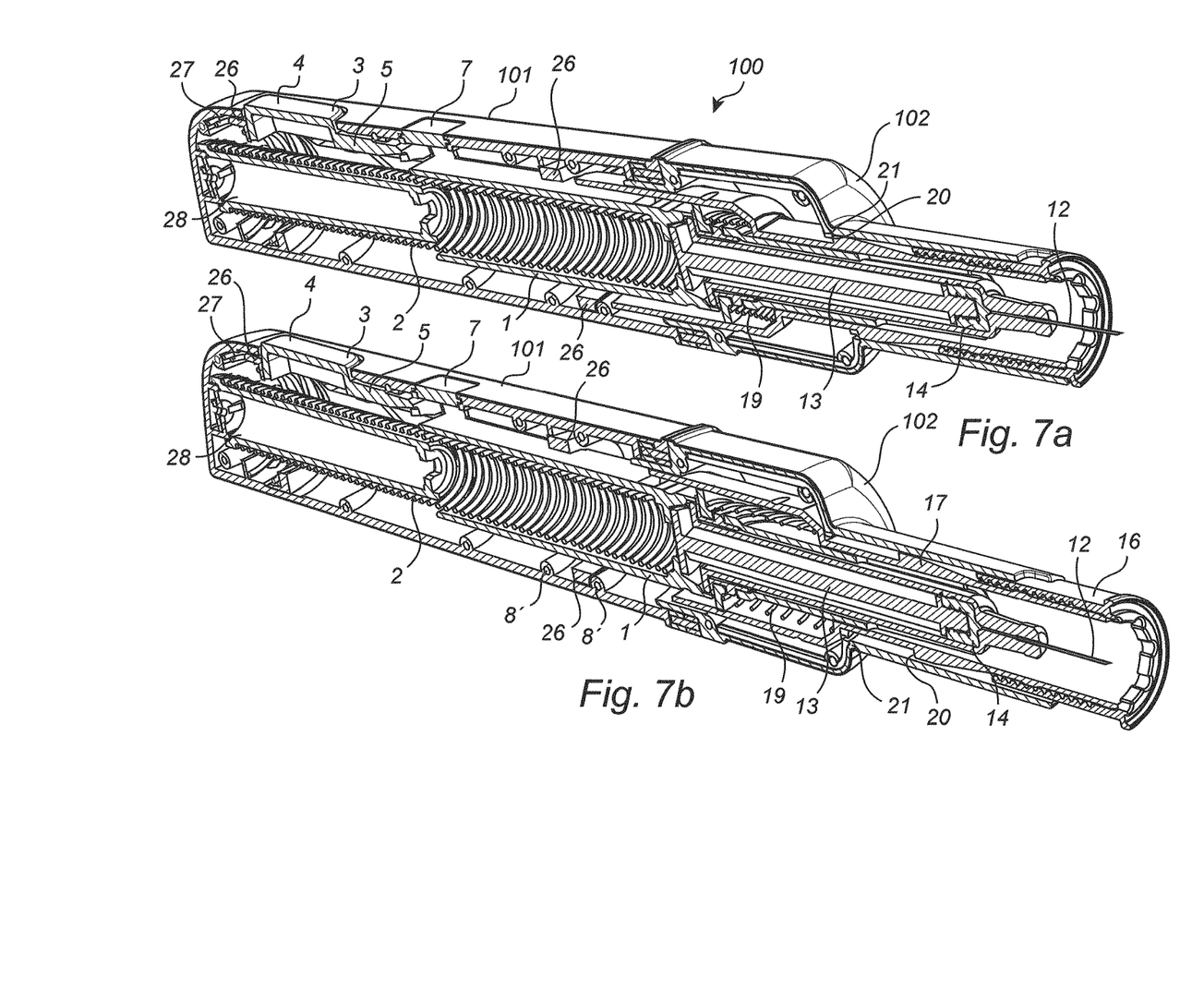

FIG. 6a shows the device loaded with a fresh syringe and in a cocked position, i.e. drive spring 2 is completely compressed such that the drive mechanism 108 is loaded but release mechanism 3 is prevented from releasing the plunger rod driver 1. This is realized by the button blocker 26 reaching from a proximal part of the rear housing 101 to a distal part of the rear housing 101 where it prevents the trigger button 4 from being depressed and releasing the drive mechanism 108. In the embodiment shown in FIGS. 6-7, the button blocker 26 is moveable between a proximal and a distal position defined by the openings 8' provided in the rear housing 101. Abutment member 5 of the release mechanism 3 (see also FIGS. 2a and 2b) reaches into recess 9 of the plunger rod driver 1 and prevents it from moving forward towards its proximal end position. The needle shield remover 109 is still in place grasping needle shield 11 and it can be used to set a desirable penetration depth. In FIG. 6b the needle hider front has been set in a position corresponding to maximum penetration depth and the needle shield remover 109 has subsequently been pulled out together with the needle shield 11. The device 100 is now in position corresponding to when a user presses it against the intended injection site by which the needle hider body 17 and needle hider front 16, have assumed the distal end position, where abutment surfaces 20, 21 come in contact with each other. Upon pressing the device against the injection site, the needle hider body 17 also comes into contact with the button blocker 26. As the needle hider body 17 travels backwards, towards the distal end position, it forces the button blocker 26 axially relative to the rear housing towards a distal end position. This movement of the button blocker 26 allows the release mechanism 3 to be activated and the device 100 is now ready to start the injection. In FIG. 7a the trigger button 4 has been depressed, causing the plunger rod driver 1 to be forced forwards by drive spring 2 and thereby moving the syringe 103 and syringe guide 24 towards the proximal end position of the syringe guide 24. As the syringe 103 and syringe guide 24 move forward, needle 12 penetrates the injection site and the plunger rod 13 forces the plunger 14 forward thus emptying the content of the syringe through the opening in the needle. The force of the drive spring 2 is far more powerful than that of the first biasing member 19 which therefore is compressed when the drive mechanism 108 is released. FIG. 7b corresponds to a state where a user has removed the device from the injection site after completed injection. As soon as this is done, the first biasing member 19 extends and needle hider body 17 assumes its proximal end position thus effectively hiding the needle 12 from being visible to a user. A second biasing member 27 is provided between the rear housing 101 and the button blocker 26 which, when the drive mechanism 108 is forced to its distal end position and the release mechanism assumes its extended position (see description referring to FIGS. 2a and 2b), will force the button blocker 26 to assume its proximal end position thus preventing the trigger button 4 from being depressed. Also shown in e.g. FIG. 6a is a spring guide 28 which supports and guides drive spring 2 in order to avoid buckling of drive spring 2 during compression.

Finally, it is realized, that a medicament injection device according to the invention has a number of advantages over the known prior art devices. Due to the fact that the device has a completely mechanical design, reliability can be ensured at all time without being dependent on batteries or similar. The drive mechanism can in a simple and reliable manner be reloaded by using the front housing and the needle shield remover of the device itself. The needle hider front is biased and always covers the needle such that the needle never will be visible to the patient. Penetration depth can also be set in a very simple and user-friendly manner. By using the needle shield remover as a grip, also users with reduced strength and/or co-ordination will be able to do this. The indication means of the present invention will in a clear and concise manner present a set penetration depth. The set penetration depth will not have to be re-set for each injection occasion; instead the device according to the present invention provides an automatic penetration depth memory. The device is re-usable and the user can change the emptied syringe to a new in a simple manner. The device allows for a variable penetration depth and the setting of the dose can be set downwardly and upwardly until a required depth has been set.

It is to be understood that the embodiments described above and in the drawings are to be regarded only as non-limiting examples of the invention and that they may be modified in many ways within the scope of the claims.

The invention claimed is:

1. A medicament injection device configured to receive a replaceable container subassembly having a medicament container with a plunger therein, a needle, and a needle shield, the medicament injection device having proximal and distal ends and comprising:
   a front housing and a rear housing releasably connected to each other;
   a reloadable drive mechanism disposed in the rear housing and configured to act on a replaceable container subassembly received in the medicament injection device, the reloadable drive mechanism being movable between a cocked position and an extended position;

a release mechanism configured to release the drive mechanism from the cocked position to the extended position;

a needle hider body disposed in the front housing;

a needle hider front slidably arranged in the front housing and adjustably connected to the needle hider body by a threaded connection; and a needle shield remover configured to connect to the needle shield, wherein the needle shield remover is removably inserted into a proximal end of the front housing through the needle hider front and, when inserted into the proximal end of the front housing, interacts with the reloadable drive mechanism such that a user can move the reloadable drive mechanism from the extended position to the cocked position;

wherein the needle shield remover and the needle hider front are configured to mate with each other such that axial movement of the needle shield remover relative to the needle hider front is permitted and rotation of the needle shield remover relative to the needle hider front is prevented.

2. The medicament injection device of claim 1, wherein the needle hider body is axially movable within the front housing between a proximal end position and a distal end position; a syringe guide within the needle hider body receives a replaceable container subassembly received in the medicament injection device, the syringe guide being axially movable between a proximal end position and a distal end position relative to the front housing; and a proximal end surface of the syringe guide determines a maximum insertion depth for the needle shield remover.

3. The medicament injection device of claim 2, further comprising a first biasing member arranged between the syringe guide and the needle hider body, wherein the first biasing member biases the syringe guide toward the distal end position and the needle hider body toward the proximal end position.

4. The medicament injection device of claim 2, further comprising a resilient syringe collar arranged at a distal end of the syringe guide, wherein the resilient syringe collar is configured to receive and hold a replaceable container subassembly received in the medicament injection device.

5. The medicament injection device of claim 2, wherein the front housing comprises internal abutment surfaces that determine the proximal end positions and distal end positions of the needle hider body and the syringe guide.

6. The medicament injection device of claim 2, wherein the rear housing comprises a button blocker that is movable between a proximal end position, in which the button blocker prevents the release mechanism from releasing the drive mechanism from the cocked position to the extended position, and a distal end position, in which the button blocker allows the release mechanism to release the drive mechanism from the cocked position to the extended position; and the button blocker moves from the proximal end position to the distal end position when the needle hider body axially moves within the front housing from the proximal end position to the distal end position.

7. The medicament injection device of claim 6, further comprising a second biasing member in the rear housing that biases the button blocker toward the proximal end position.

8. The medicament injection device of claim 1, wherein a penetration depth of a needle of a replaceable container subassembly received in the medicament injection device is adjusted by adjusting a position of the needle hider front.

9. The medicament injection device of claim 1, wherein the needle hider front comprises an indicator configured to indicate a set penetration depth of a needle of a replaceable container subassembly received in the medicament injection device.

10. The medicament injection device of claim 1, wherein the needle shield remover comprises a flexible hook device configured to grasp the needle shield of a replaceable container subassembly received in the medicament injection device.

11. The medicament injection device of claim 10, wherein the plunger rod driver acts on the plunger of a replaceable container subassembly received in the medicament injection device to move the replaceable container subassembly axially in relation to the front housing such that the needle is penetrated and medicament is expelled through the needle.

12. The medicament injection device of claim 1, wherein the reloadable drive mechanism comprises an axially movable plunger rod driver and a drive spring that biases the plunger rod driver toward a proximal end position, and the plunger rod driver and the rear housing include corresponding guides that guide the plunger rod driver during movement in the rear housing.

13. A method of reloading a medicament injection device according to claim 1, comprising:
    removing, through the needle hider front, the front housing from the rear housing having the needle shield remover arranged at the front housing;
    bringing the proximal end of the needle shield remover into contact with a proximal end of the reloadable drive mechanism in the rear housing; and
    subsequently pushing the front housing and the needle shield remover axially toward the rear housing and the drive mechanism, thereby moving the reloadable drive mechanism from the extended position to the cocked position.

* * * * *